United States Patent [19]

Brazdil, Jr. et al.

[11] Patent Number: 4,866,195
[45] Date of Patent: Sep. 12, 1989

[54] METHOD FOR AMMOXIDATION OF PARAFFINS AND CATALYST SYSTEM THEREFOR

[75] Inventors: James F. Brazdil, Jr., Mayfield Village; Linda C. Glaeser, Cleveland Hts.; Mark A. Toft, Lakewood, all of Ohio

[73] Assignee: The Standard Oil Company, Cleveland, Ohio

[21] Appl. No.: 234,644

[22] Filed: Aug. 22, 1988

Related U.S. Application Data

[62] Division of Ser. No. 111,829, Oct. 22, 1987, Pat. No. 4,801,568.

[51] Int. Cl.$^4$ .............................................. C07C 120/14
[52] U.S. Cl. .................................................... 558/319
[58] Field of Search ........................................ 558/319

[56] References Cited

U.S. PATENT DOCUMENTS

| | | | |
|---|---|---|---|
| 4,035,410 | 7/1977 | Marion et al. | 502/242 X |
| 4,316,855 | 2/1982 | Graselli et al. | 502/215 |

*Primary Examiner*—Joseph Paul Brust
*Attorney, Agent, or Firm*—C. S. Lynch; D. J. Untener; L. W. Evans

[57] ABSTRACT

Ammoxidation of $C_3$ to $C_5$ acyclic alkanes with $NH_3$ and $O_2$ using (1) a mole ratio of alkane:$NH_3$ in the range from 2 to 16 and a mole ratio of alkane:$O_2$ in the range 1 to 10 and (2) a mixture of particulate catalyst compositions, the first being especially effective to promote formation of an unsaturated nitrile and an olefin from the paraffin, and the second catalyst composition being especially effective to promote the conversion of the olefin to the unsaturated nitrile. Catalytic compositions useful in the process are disclosed.

18 Claims, No Drawings

METHOD FOR AMMOXIDATION OF PARAFFINS AND CATALYST SYSTEM THEREFOR

This is a divisional of co-pending application Ser. No. 111,829 filed Oct. 22, 1987, now U.S. Pat. No. 4,801,568.

This invention relates to an improved process for the catalytic ammoxidation of paraffins containing from 3 to 5 carbon atoms to $\alpha,\beta$-unsaturated nitriles, especially paraffins containing 3 to 4 carbon atoms. Most important is the ammoxidation of isobutane to methacrylonitrile and, especially, of propane to acrylonitrile.

Because of the price differential between propylene and propane an economic incentive exists for the development of a viable catalytic process for conversion of propane to acrylonitrile.

Earlier attempts in the prior art to develop an efficient process for the ammoxidation of propane to acrylonitrile produced either insufficient yields or processes that necessitated adding halogen promoters to the feed. The latter procedure would require not only reactors made of special corrosion resistant materials, but also the quantitative recovery of the promoter. The added costs thus eliminated the advantage of the propane/propylene price differential.

It is thus an object of the present invention to provide an improved process for the ammoxidation of paraffins to unsaturated nitriles.

It is a further object of the invention to provide new catalyst systems for such process.

Still another object is to provide an improved catalytic ammoxidation process for making unsaturated nitriles from lower paraffins without the use of halogen promoters.

Other objects, as well as aspects, features and advantages, of the present invention will become apparent from a study of the accompanying disclosure and the claims.

The foregoing and other objects of the present invention are achieved by the process of the present invention. There are two main features of the present process invention. The first of these is the use of an excess of the alkane feed with relation to $NH_3$ and molecular oxygen. The second feature, which is used in combination with the high ratio of the $C_3$ to $C_5$ paraffin to $NH_3$ and $O_2$, is that a combination, i.e., a mixture, of catalysts is employed, the first catalyst composition being especially effective to promote formation of an unsaturated nitrile and an olefin from the paraffin, and the second catalyst composition being especially effective to promote the conversion of the olefin to the unsaturated nitrile. Such mixture is the subject of the composition claims herein.

In the present application "paraffin" designates an acyclic paraffin.

British patent specifications 1,336,135 and 1,336,136 disclose the use of high ratios of propane or isobutane to ammonia and oxygen, but only single ammoxidation catalysts are used, and the yields of acrylonitrile are extremely poor. U.S. Pat. No. 3,860,534 also discloses use of such high ratios, using a catalyst containing only V and Sb oxides. However, after the catalyst is calcined, it is washed for 24 hours with water and dried, a laborious procedure. A. N. Shatalova et al. in Neftekhiniya 8, No. 4, 609–612 (1968), describe the reaction of propane with oxygen and ammonia using a large excess of propane and a mixture of two catalysts, one of which is described as oxides of metals having dehydrogenating characteristics at 550° and 600° C. At 500° C. little or no acrylonitrile was produced. Rather large amounts of propionitrile and acrolein were made per mole of acrylonitrile produced. The per pass conversion of propane to acrylonitrile was generally 2–4 percent with selectivity to acrylonitrile being from 12 to 33 percent.

In the present process when applied to propane ammoxidation a small amount of propylene is produced in relation to the unreacted propane in the effluent. Such propane effluent containing propylene in the amount of up to 8 mole percent, but usually no more than 6 mole percent, of the amount of propane plus propylene can comprise the substrate feed to the present process. And in general the $C_3$ to $C_5$ alkane feed to the process can contain one or more $C_3$ to $C_5$ olefins. The $C_3$ to $C_5$ olefin content of the feed to the present ammoxidation process can contain from zero to 8 mole percent of such olefin(s), based on the moles of $C_3$ to $C_5$ paraffin plus olefins fed, and this feed can be from any source. Although larger amounts of $C_3$ to $C_5$ olefins may be present in the substrate paraffin feed, usual amounts are as stated, and the usual olefin is that corresponding to the particular paraffin fed to the reaction zone of the present process.

According to the present invention there is provided a process for the ammoxidation of a $C_3$ to $C_5$ paraffin which comprises contacting in a reaction zone said paraffin in the vapor phase in admixture with ammonia, molecular oxygen, and optionally an inert gaseous diluent, with an intimate particulate mixture of a first catalyst composition and a second catalyst composition, said feed to the reaction zone containing a mole ratio of paraffin:$NH_3$ in the range from 2 to 16 (usually 3–7), and a mole ratio of paraffin to $O_2$ in the range from 1 to 10 (usually 1.5–5), said first catalyst composition being 10–99 weight percent of a diluent/support of 90–1 weight percent of a catalyst having the components in the proportions indicated by the empirical formula:

$$VSb_mA_aH_bC_cT_tO_x, \quad \text{formula (1)}$$

where

A is one or more of W, Sn, Mo, B, P and Ge;

H is one or more of Fe, Co, Ni, Cr, Pb, Mn, Zn, Se, Te, Ga, In and As;

C is one or more of an alkali metal and Tl;

T is one or more of Ca, Sr and Ba; and where m is from 0.01 and up to 20; a is 0.1–10; b is 0–20; c is 0–20 (usually 0–1); t is 0–20; the ratio (a+b+c+5):(1+m) is 0.01–6; wherein x is determined by the oxidation state of the other elements, and wherein the antimony has an average valency higher than +3 and the vanadium has an average valency lower than +5, said second catalyst composition being 0–99 weight percent of a diluent/support and 100–1 weight percent of a catalyst having the components in the proportions indicated by the empirical formulas:

$$A_aC_cG_gSn_dSb_eO_x \quad \text{formula (2)}$$

where

A is one or more of Cu, V, W, Mo

C is one or more of Bi, Ti, Ge, La, Ce, Cr, Mn, Mg Ca, Co, Ni, Pb, Nb, Ta, Zr, Ag, Zn, Cd, B, P, Ga, In, Te, Fe, Sm G is one or more of K, Cs and Na a is 0–10 c is 0–10 d is 0.1–10 e is 0.1–10 g is 0–1

(d+e) is 5–20 x is a number determined by the requirements of the other elements present, and wherein the atoms of V:e is <0.01, the atoms of V:d is <0.01, the atoms of Fe are either less than d or are less than e, and wherein the weight ratio in said mixture of said first catalyst composition to said second catalyst composition is in the range of 0.001 to 2.5.

In an especially useful catalyst of formula (1), m is greater than 1 (often 2–10, more often 3–7).

By "particulate mixture" as used herein is meant a mixture of solid particles or subdivided pieces of the first catalyst composition with separate and distinct solid particles of the second catalyst composition. The particles are often of a size used in fluidized bed reactors, say about 40 to 90 microns, but of course larger particles of catalyst can be employed for use in fixed or gravity flowing catalyst beds.

In the present process in all its embodiments the ratio of $O_2$ to $NH_3$ fed to the reaction zone is usually in the range from 1 to 10 (more often 1–5) and the ratio of inert gaseous diluent to paraffin is usually in the range zero to 5 (more often zero to 3).

The diluent or support for either catalyst composition is a refractory metal oxide or mixture, such as silica, silica-alumina, etc.

In the usual practice of the present invention the catalyst support/diluent for the catalyst of formula (1) is not an oxide of an element named in formula (1). Further, in the usual practice of the invention the catalyst support/diluent for the catalyst of formula (2) is not an oxide of an element named in formula (2).

In the catalyst compositions of the invention the catalyst empirical formulas (1) and (2) do not, of course, connote any particular chemical compound, nor indicate whether the elements are present as a mixture of individual oxides or as a complex oxide or oxides, or what separate crystalline phases or solid solutions may be present. Similarly, the designation of certain oxides, such as "silica" or "alumina" or $SiO_2$ or $Al_2O_3$, as supports or diluents is merely in accordance with convention in the inorganic oxide catalyst art, and such designations refer to compounds often regarded as supports in the catalyst art. Such designations, however, do not mean that the element involved is actually present as a simple oxide. Indeed, such elements may at times be present as a complex oxide with one, more than one, or all of the elements in formula (1) or formula (2), which complex oxides form during the precipitation or agglomeration, drying and calcining process for preparing the catalyst composition.

The process of the invention is especially useful in the ammoxidation of propane or isobutane.

According to the present invention the foregoing first catalyst composition is prepared under conditions such that in the final composition the average oxidation state of vanadium is less than 5.

One method for preparing the first catalyst composition is by a redox reaction between a compound of trivalent antimony such as $Sb_2O_3$ and a compound of pentavalent vanadium such as $V_2O_5$, during which the antimony is oxidized and the vanadium reduced.

The foregoing redox reaction was described by Birchall and Sleight (*Inorganic Chem.* 15, 868–70 [1976]) and by Berry et al. (*J. Chem. Soc. Dalton Trans.*, 1983, 9–12), who effected the reaction by heating a dry mixture of the above reactants at temperatures above 600° C. This product had a tetragonal rutiletype crystalline structure with a unique x-ray diffraction pattern.

However, it has been found that the redox reaction can successfully and more conveniently be carried out in an aqueous medium by heating at a temperature of at least 80° C. and up to 200° C., for instance, by heating an aqueous dispersion of a $V^{5+}$compound, such as $NH_4VO_3$ or $V_2O_5$, with an $Sb^{3+}$compound, such as by reacting $Sb_2O_3$ and $NH_4VO_3$ (or $V_2O_5$). This step is followed by evaporation, drying and then calcining the product in a molecular oxygen-containing atmosphere, such as air, at from 350° to 700° or 750° C., usually 400° to 650° C. The length of the calcination period may range from 30 minutes to 12 hours, but satisfactory catalyst compositions are usually obtained by calcination at such temperatures for a period of from 1 to 5 hours.

At least part of any excess of trivalent antimony compound, such as $Sb_2O_3$, is usually oxidized to $Sb_2O_4$ during the calcination in a molecular oxygen-containing atmosphere, such as air.

The ingredients of the first catalyst composition other than vanadium and antimony (and of course part of the oxygen) suitably can be incorporated after completion of the foregoing redox reaction. Thus, the additives A, H, C and/or T, if any, can be added in the slurry after the redox reaction, or the solid particles containing the vanadium and antimony values after separation from the aqueous medium can be coated or impregnated in a known manner with such additives at any suitable stage prior to final calcination of the catalyst, by methods generally known in the art, using oxides, hydroxides, acids, salts (particularly organic salts such as acetates), and other compounds of such elements.

In formula (1) subscript a usually is at least 0.4 or 0.5. In formula (1) at least 0.2 atoms of W are susally present per atom of V, and the total of W plus Sn atoms (if any Sn is present) is usually at least 0.4 atoms. Preferred compositions of formula (1) contain at least 0.4 atoms of W per atom of V. Particularly when W is present, is it especially useful to have at least 0.4 atoms of P per atom of V in addition to the W. Especially useful are such compositions wherein said diluent/support comprises 20–100weight percent alumina and 80 to zero weight percent silica.

Especially useful catalysts of formula (1) description are those in which a is at least 1, wherein A includes at least 1 atom of W.

Not only does the catalyst support in the first catalyst composition (formula (1)) improve mechanical stability of the catalyst, but also the catalytic activity is significantly improved, especially in the case of alumina and silica-alumina. Besides alumina and silica-alumina other supports that can be used are silica, titania, silica-titania, $Nb_2O_5$, silica-niobia, silica-zirconia, zirconia and magnesia, etc.

In the first catalyst composition, now preferred support materials for not only improving mechanical stability but also for improving the yield of the desired nitriles are selected from silica-alumina and alumina having 20–100, usually 50–100, preferably 60–100 weight percent alumina; silica-titania and titania having 20–100 weight percent titania; silica-zirconia and zirconia having 80–100 weight percent zirconia; and silica-niobia and niobia having 30–100 weight percent niobia ($nb_2O_5$).

In the preparation of the second catalyst composition of formula (2) the metal oxides can be blended together or can be formed separately and then blended or formed separately or together in situ. Promoter oxides, if any, are preferably incorporated into the tin-antimony based catalyst by blending into the gel before calcining or by blending into the oven-dried base catalyst before calcining. A preferred manner of incorporating promoter elements is by choosing a water-soluble salt of the promoter element, forming an aqueous solution of the salt, and mixing the solution with a solution or a suspension of the base elements or salts thereof. Optionally, the promoter elements can be incorporated by the use of soluble complex salts or compounds with the desired base elements which upon calcination will yield the desired ratio of the elements in the finished catalyst.

To introduce the tin component into the catalyst one may conveniently use an $SnO_2$ sol. Antimony is suitably introduced as $Sb_2O_3$, or an $Sb_2O_5$ sol can be used. It is also possible to add finely divided antimony metal to concentrated nitric acid and then to boil the slurry to decompose the excess nitric acid, leaving an antimony oxide slurry.

Other variations in starting materials will suggest themselves to one skilled in the art, particularly when the preferred starting materials mentioned hereinabove are unsuited to the economics of large-scale manufacture. In general, any compounds containing the desired catalyst components may be used provided that they result, upon heating to a temperature within the range disclosed hereinafter, in the oxides of the instant catalyst.

These second catalyst compositions are conveniently prepared by slurry techniques wherein an aqueous slurry containing all of the elements in the objective catalyst is produced, the water removed from the aqueous slurry to form a precatalyst precipitate or powder and the precatalyst then heated in the presence of an oxygen-containing gas such as air at elevated temperature to calcine the precatalyst thereby forming the catalyst. Liquids other than water, such as $C_1$ to $C_8$ alcohols can also be used to form the precatalyst slurry.

In the second catalyst composition the support can be any of the usual supports such as silica, alumina or silica-alumina, and the like.

In the ammoxidation of the present invention, the reaction is carried out in the gas phase by contacting a mixture of the paraffin, ammonia and molecular oxygen, and inert diluent, if any, conveniently in a fixed bed of the catalyst mixture, or a gravity flowing bed, a fluidized bed or a fast transport reactor mode.

Examples of inert diluents useful in the reaction are $N_2$, He, $CO_2$, $H_2O$ and Ar.

The reaction temperature range can vary from 350° to 700° C., but is usually 430° to 520° C. The latter temperature range is especially useful in the case of propane ammoxidation to acrylonitrile.

The average contact time can often be from 0.01 to 10 seconds, but is usually from 0.02 to 10 seconds, more usually from 0.1 to 5 seconds.

The pressure of the reaction usually ranges from 2 to 45 psia. Most often, pressure is somewhat above atmospheric.

The following examples of the invention are exemplary and should not be taken as in any way limiting.

EXAMPLE 1

A catalyst having the composition 60 wt % $Cr_2Cu_{3.8}Te_{1.7}W_{0.2}Mo_{0.5}Sn_{30}Sb_{18}Cs_{0.05}B_{0.5}O_x$—40 wt % $SiO_2$ was made as follows: 91 g of a 12 wt % $Sb_2O_5$ sol was added to 208.2 g of a 40 wt % $SiO_2$ sol; 91 g of the $Sb_2O_5$ sol was added to 376.8 g of an 18 wt % $SnO_2$ sol with heating and the two mixtures were combined. 12.01 g of $Cr(NO_3)_3 \cdot 9H_2O$, 13.26 g of $Cu(NO_3)_2 \cdot 2.5$ $H_2O$ and 1.46 g of a 10 wt % $CsNO_3$ solution were added to another 121 g of the $Sb_2O_5$ sol, and the pH was adjusted to about 6 and the mixture stirred. This latter mixture was then added to the Sn/Sb/Si mixture.

0.82 g ammonium metatungstate (85% $WO_3$ equivalent) and 1.32 g. of $(NH_4)_6Mo_7O_{24} \cdot 4H_2O$ were dissolved in water and then some of the total of 3.25 g of Te metal to be added was introduced with about 12 ml of $H_2O_2$. Then 12 ml more of $H_2O_2$ were added, and then the balance of the 3.25 g of Te metal was added. The mixture began to bubble, producing a clear yellow solution. This was added to the above mixture, together with 0.46 g of $H_3BO_3$ and 61 g of a 12 wt % $Sb_2O_5$ sol. The mixture was then digested with heating and stirring. Its pH was about 7.5. The mixture was evaporated to dryness, heated at 290° C. for 3 hours, 425° C. for 3 hours, ground and screened to 20/35 mesh and then heated 875° C. for 3 hours.

EXAMPLE 2

A catalyst having the composition $SbSn_3ti_{0.4}O_x$ was made as follows:

388.92 gms. of an 18% $SnO_2$ sol was added to 208.74 gms of a 12% $Sb_2O_5$ sol with stirring. Then 21.08 gms of tetrabutoxytitanium was added and the mixture was stirred and heated until it became thick. It was dried in an oven at 130° C. overnight, then heated 3 hours at 290° C., 3 hours at 425° C., ground and screened to 20–35 mesh and heated 3 hours at 610° C.

EXAMPLE 3

A catalyst having the composition 60 wt % $Cr_{0.5}Cu_{3.8}Te_{1.7}W_{0.7}Sn_{30}Sb_{18}O_x$—40 wt % $SiO_2$ was made.

2.86 g of ammonium metatungstate (85 wt % $WO_3$ equivalent) was dissolved in about 25 ml of $H_2O$. Then some of the 3.25 g Te metal ultimately to be used was added to the tungsten solution with heating and stirring. Then a total of 50 ml $H_2O_2$ was added in 10 mil aliquots until bubbling was observed. Then the remainder of the 3.25 g Te metal was added in small increments with continued bubling until the solution turned clear.

376.8 g of an 18 wt % $SnO_2$ was added to 364.0 g of a 12 wt % $Sb_2O_5$ sol in a beaker, and then 216.15 g of a 40 wt % $SiO_2$ sol was added to the beaker. To this was then added the previously prepared clear solution containing the Te and W values.

12.01 g of $Cr(NO_3)_3 \cdot 9H_2O$ was dissolved in about 20 ml $H_2O$, and 13.26 g of $Cu(NO_3)_2 \cdot 2.5 \ H_2O$ was added to about 30 ml $H_2O$. The Cr and Cu dispersions were then combined and then slowly added to the beaker with additional water. The total volume was about 1900 ml. The pH of the resulting slurry was about 5.5. The slurry was evaporated to dryness, and the solid heated for 3 hours at 290° C. and for 3 hours 425° C., the ground to 20–35 mesh, and finally calcined by heated for 3 hours at 875° C.

EXAMPLE 4

A catalyst having the empirical formula 50 wt % $VSb_{3.5}P_{0.5}WO_x$ + 50 wt % $Al_2O_3$ support was made as follows:

In a stirred flask equipped for heating under reflux, 3.81 g $NH_4VO_3$ were dissolved in 90 ml hot water. To the hot solution 16.6 g $Sb_2O_3$ were added, and the slurry was boiled under reflux for 16-18 hours overnight. There was ammonia evolution, and the vanadium antimony mixture turned gray-green.

In a separate operation, 35.3 g Catapal SB (hydrated alumina) were mixed with 127.2 ml $H_2O$ (cold) +14.1 g acetic acid (10 percent solution) and stirred until the suspension gelled. It took about 3 hours, and the gel was soft, homogeneous, with the consistency of thick cream.

Meanwhile, the vanadium antimony slurry was transferred to a beaker. A solution of 8.80 g ammonium meta-tungstate in about 20 ml $H_2O$ and a solution of 1.77 g $(NH_4)_2HPO_4$ in $H_2O$ were then added, followed by the addition, with stirring (magnet) of the alumina gel. After partial evaporation, the mixture became too thick for stirring. It was then transferred to an evaporating dish, and the evaporation, following by drying overnight, was continued in an oven at 110-120° C. The dried material was precalcined at 350° C. for 5 hours, screened to 20/35 mesh, then calcined 3 hours at 610° C.

EXAMPLE 5

A catalyst having the empirical formula 45 wt % $VSb_{3.5}P_{0.5}WO_x + 55$ wt % $Al_2O_3$ support was made as follows:

In a stirred flask, 7.07 g of ammonium metatungstate and 3.03 g $NH_4VO_3$ were dissolved in 200ml hot water, and 1.49 g of 85% $H_3PO_4$ was added. To the hot solution 13.22 g $Sb_2O_3$ were added, and the slurry was stirred and heated for about 1 hours.

In a separate operation, 32.35 g Catapal SB (hydrated alumina) were mixed with 120 ml $H_2O$ (cold) +5.5 g acetic acid (10 percent solution) and stirred for 1 hours. The resulting dispersion was added to the other mixture with stirring. The resulting slurry was partially evaporated on a hotplate, followed by drying overnight in an oven at 110°-120° C. The dried material was precalcined at 350° C. for 5 hours, screened to 20/35 mesh, then calcined 3 hours at 610° C.

In the ammoxidation runs of the following examples, the catalyst, or the mixture of catalysts, is in a tubular ⅜ inch I.D. stainless steel fixed bed reactor. When a mixture of particulate catalysts is used, as in the invention examples, the desired weight of each of the two catalyst compositions is put in a vial and shaken until uniformly dispersed before placing the desired amount of the catalyst mixture in the reaction tube. The reaction is equipped with a preheat leg and is immersed in a temperature controlled molten salt bath. The gaseous feed components are metered through mass flow controllers into the bottom of the reactor through the preheat leg. Water is introduced through a septum at the top of the preheat leg, using a syringe pump. The feed is fed to the catalyst for 1 hour before collection of product; the runs of each example last 30-60 minutes during which the product is collected for analysis.

EXAMPLE 6

In this example the catalyst was a mixture of the catalyst of Example 2 and the catalyst of Example 4 in the weight ratio of the latter to the former of 0.15. The reaction temperature was 470° C. and the molar feed ratios were 5 propane/1 $NH_3$/2 $O_2$/1 $H_2O$. The contact time was 0.8 seconds. Analysis of the reactor effluent showed that propane conversion was 13.1 percent; yield and selectivity of propane to acrylonitrile were 5.9 and 44.8 percent, respectively; selectivity to propylene was 22.7 percent; selectivity to HCN was 8.9 percent.

COMPARATAIVE EXAMPLE A

In this example the reaction temperature was 470° C. and the molar feed ratios were 5 propane/1 $NH_3$/2 $O_2$/1 $H_2O$. The catalyst was the catalyst of Example 2 alone. The contact time was 0.5 seconds. Analysis of the reactor effluent showed that propane conversion was only 3.0 percent; yield and selectivity of propane to acrylonitrile were 1.3 and 42.2 percent respectively; selectivity to propylene was 15.9 percent; selectivity to HCN was 16.6 percent.

EXAMPLE 7

In this example the catalyst was a mixture of the catalyst of Example 2 and the catalyst of Example 5 in the weight ratio of the later to the former of 0.105. The reaction temperature was 470° C. and the molar feed ratios were 5 propand/1 $NH_3$/2 $O_2$/1 $H_2O$. The contact time was 1.2 seconds. Analysis of the reactor effluent showed that propane conversion was 13.5 percent; yield and selectivity of propane to acrylonitrile were 5.8 and 43.0 percent, respectively; selectivity to propylene was 15.8 percent; selectivity to HCN was 7.8 percent.

EXAMPLE 8

In this example the catalyst was a mixture of the catalyst of Example 1 and the catalyst of Example 4 in the weight ratio of the latter to the former of 0.15. The reaction temperature was 470° c. and the molar feed ratios were 5 propane/1 $NH_2$/2 $O_2$/1 $H_2O$. The contact time was 1.6 seconds. Analysis of the reactor effluent showed that propane conversion was 12.4 percent; yield and selectivity of propane to acrylonitrile were 4.9 and 39.4 percent, respectively; selectivity to propylene was 31.8 percent; selectivity to HCN was 5.4 percent.

EXAMPLE 9

In this example the catalyst was a mixture of the catalyst of Example 3 and the catalyst of Example 4 in the weight ratio of the latter to the former of 0.15. The reaction temperature was 470° C. and the molar feed ratios were 5 propane/1 $NH_3$/2 $O_2$/1 $H_2O$. The contact time was 1.5 seconds. Analysis of the reactor effluent showed that propane conversion was 12.2 percent; yield and selectivity of propane to acrylonitrile were 4.0 and 33.0 percent, respectively; selectivity to propylene was 37.3 percent; selectivity to HCN was 8.4 percent.

EXAMPLE 10

In this example the catalyst was a mixture of the catalyst of Example 1 and the catalyst of Example 4 in the weight ratio of the latter to the former of 0.15. The reaction temperature was 470° C. and the molar feed ratios were 5 propane/1 $NH_3$/2 $O_2$/1 $H_2O$. The contact time was 1.6 seconds. Analysis of the reactor effluent after a pre-run of 24 hours showed that propane conversion was 10.1 percent; yield and selectivity of propane to acrylonitrile were 3.9 and 38.7 percent, respectively; selectivity to propylene was 35.1 percent; selectivity to HCN was 8.4 percent.

EXAMPLE 11

In this example the catalyst was a mixture of the catalyst of Example 2 and the catalyst of Example 4 in the weight ratio of the latter to the former of 0.15. The reaction temperature was 470° C. and the molar feed ratios were 5 propane/1 $NH_3$/2 $O_2$/1 $H_2O$. The contact time was 1.5 seconds. Analysis of the reactor effluent after a pre-run of 24 hours showed that propane conversion was 9.2 percent; yield and selectivity of propane to acrylonitrile were 2.9 and 31.6 percent, respectively; selectivity to propylene was 40.7 percent; selectivity to HCN was 10.0 percent.

As will be evident to those skilled in the art various modifications of this invention can be made or followed in the light of the foregoing disclosure and discussion without departing from the spirit and scope of the disclosure or from the scope of the claims.

We claim:

1. A process for the ammoxidation of A $C_3$ to $C_5$ paraffin to an $\alpha,\beta$-unsaturated nitrile which comprises contacting in a reaction zone said paraffin in the vapor phase in admixture with ammonia, molecular oxygen, and optionally an inert gaseous diluent, with an intimate particulate mixture of a first catalyst composition and a second catalyst composition, said feed to the reaction zone containing a mole ratio of paraffin:$NH_3$ in the range from 2 to 16 and a mole ratio of paraffin to $O_2$ in the range from 1 to 10, said first catalyst composition being 10–99 weight percent of a diluent/support and 90–1 weight percent of a catalyst having the components in the proportions indicated by the empirical formula:

$$VSb_mA_aH_bC_cT_tO_x, \qquad \text{formula (1)}$$

where

A is one or more of W, Sn, Mo, B, P and Ge and includes at least 0.2 atoms of W per atom of V;

H is one or more of Fe, Co, Ni, Cr, Pb, Mn, Zn, Se, Te, Ga, In and As;

C is one or more of an alkali metal and Tl;

t is one or more of Ca, Sr and Ba; and where m is from 0.01 and up to 20; a is 0.2–10; b is 0–20; c is 0–1; t is 0–20; the ratio $(a+b+c+t):(1+m)$ is 0.01–6; wherein X is determined by the oxidation state of other elements, and wherein the antimony has an average valency higher than $+3$ and the vanadium has an average valency lower than $+5$, said second catalyst composition being 0–99 weight percent of a diluent/support and 100–1 weight percent of a catalyst having the components in the proportions indicated by the empirical formula:

$$A_aC_cG_gSn_dSb_eO_x \qquad \text{formula (2)}$$

where

A is one or more of Cu, V, W, Mo

C is one or more of Bi, Ti, Ge, La, Ce, Cr, Mn, Mg Ca, Co, Ni, Pb, Nb, Ta, Zr, Ag, Zn, Cd, B, P, Ga, In, Te, Fe, Sm G is one or more of K, Cs and Na A is 0–10 c is 0–10 d is 0.1–10 e is 0.1–10 g is 0–1

(d+e) is 5–20 x is a number determined by the requirements of the other elements present, and wherein the atoms of V:e is $<0.01$, the atoms of V:d is $<0.01$, the atoms of Fe are either less than d or are less than e, and wherein the weight ratio in said mixture of said first catalyst composition to said second catalyst composition is in the range of 0.001 to 2.5.

2. A process of claim 1 wherein said mole ratio of paraffin:$NH_3$ is in the range from 3 to 7.

3. A process of claim 1 wherein said mole ratio of paraffin:$O_2$ is in the range from 1.5 to 5.

4. A process of claim 2 wherein said mole ratio of paraffin:$O_2$ is in the range from 1.5 to 5.

5. A process according to claim 1 wherein the mole ratio of $O_2$ to $HN_3$ in the feed to the reaction zone is in the range from 1 to 10.

6. A process according to claim 1 wherein the mole ratio of inert gaseous diluent to paraffin in the feed to the reaction zone is in the range from zero to 5.

7. A process of claim 1 wherein A of formula (1) includes at least 0.2 atoms of W per atom of V and the total A atoms include at least 0.4 (W atoms+Sn atoms) per atom of V.

8. A process of claim 1 wherein A of formula (1) includes a least 0.4 atoms of P per atom of V.

9. A process of claim 1 wherein said support for the catalyst of formula (1) is selected from silica, alumina, titania, silica-niobia, silica-zirconia, silica-titania, silica-alumina, $Nb_2O_5$ and magnesia.

10. A process of claim 1 wherein said support for the catalyst of formula (1) is selected from silica-alumina and alumina having 20–100 weight percent alumina; silica-titania and titania having 20–100 weight percent titania; silica-zirconia and zirconia having 80–100 weight percent zirconia; and silica-niobia and niobia having 30–100 weight percent niobia ($Nb_2O_5$).

11. A process of claim 1 wherein m is 2–10.

12. A process of claim 8 wherein m is 2–10.

13. A process of claim 1, wherein said diluent/support in said first catalyst composition comprises 20–100 weight percent alumina and 80 to zero weight percent silica.

14. A process of claim 1 wherein said diluent/support in said first catalyst composition comprises 50–100 weight percent alumina and 50 to zero weight percent silica.

15. A process of claim 1 wherein said paraffin is propane or isobutane.

16. A process of claim 1 wherein said paraffin is propane.

17. A process of claim 11 wherein said paraffin is propane or isobutane.

18. A process of claim 13 wherein said paraffin is propane or isobutane.

* * * * *

UNITED STATES PATENT AND TRADEMARK OFFICE
CERTIFICATE OF CORRECTION

PATENT NO. : 4,866,195

DATED : September 12, 1989

INVENTOR(S) : Brazdil, et al

It is certified that error appears in the above-identified patent and that said Letters Patent is hereby corrected as shown below:

Column 9, line 13, "A" should read --a--.
Column 9, line 36, "t" should read --T--.
Column 9, line 57, "A" should read --a--.

Signed and Sealed this

Third Day of July, 1990

Attest:

Attesting Officer

HARRY F. MANBECK, JR.

Commissioner of Patents and Trademarks

UNITED STATES PATENT AND TRADEMARK OFFICE
CERTIFICATE OF CORRECTION

PATENT NO. : 4,866,195

DATED : September 12, 1989

INVENTOR(S) : Brazdil, et al

It is certified that error appears in the above-identified patent and that said Letters Patent is hereby corrected as shown below:

Col. 2, line 47, delete "5" and insert therefor --t--.

Signed and Sealed this

Thirty-first Day of July, 1990

Attest:

HARRY F. MANBECK, JR.

Attesting Officer

Commissioner of Patents and Trademarks